United States Patent [19]
Glass et al.

[11] Patent Number: 5,296,125
[45] Date of Patent: Mar. 22, 1994

[54] ELECTROCHEMICAL SENSOR/DETECTOR SYSTEM AND METHOD

[75] Inventors: Robert S. Glass, Livermore; Sam P. Perone, Pleasanton; Dino R. Ciarlo, Livermore; James F. Kimmons, Manteca, all of Calif.

[73] Assignee: The United States of America as represented by the United States of Department of Energy, Washington, D.C.

[21] Appl. No.: 860,329

[22] Filed: Mar. 30, 1992

Related U.S. Application Data

[62] Division of Ser. No. 576,289, Aug. 31, 1990, Pat. No. 5,120,421.

[51] Int. Cl.$^5$ ............................................. C23C 14/00
[52] U.S. Cl. ........................ 204/153.21; 430/311; 430/312; 430/313; 430/319; 29/829
[58] Field of Search ............... 29/829; 430/311, 312, 430/313, 319; 204/153.21

[56] References Cited

U.S. PATENT DOCUMENTS

| | | | |
|---|---|---|---|
| 4,133,735 | 1/1979 | Afromowitz et al. | 204/195 G |
| 4,936,956 | 6/1990 | Wrighton | 204/153.21 |
| 4,969,468 | 11/1990 | Byers et al. | 128/642 |

Primary Examiner—John Niebling
Assistant Examiner—Arun S. Phasge
Attorney, Agent, or Firm—Henry P. Sartorio; Roger S. Gaither; William R. Moser

[57] ABSTRACT

An electrochemical detection system is described comprising in combination:
(a) a multielement, microelectrode array detector containing means for acquiring a plurality of signals;
(b) electronic means for receiving said signals and converting said signals into a readout or display providing information with respect to the nature and concentration of elements present in a solution being tested.

Also described is the means of making the above described microelectrode detector.

29 Claims, 11 Drawing Sheets

ELECTROCHEMICAL SENSOR/DETECTOR SYSTEM AND METHOD

The United States Government has rights in this invention pursuant to Contract No W-7405-ENG-48 between the U.S. Department of Energy and the University of California for the operation of Lawrence Livermore National Laboratory.

Division of application Ser. No. 07/576,289 filed Aug. 31, 1990 now U.S. Pat. No. 5,120,421.

FIELD OF THE INVENTION

The present invention relates principally to a system for sensing or detecting various elements and compounds in the environment and in laboratory solutions, and to a method for making a component thereof.

More specifically, the invention relates to a compact, hand-held electrochemical sensor device using, as the principle sensing element, multielement arrays of microelectrodes for sensing elements and compounds in solutions and in the environment.

The invention also relates to a method of detecting and measuring the amounts of elements and substances in solutions and in the environment utilizing the system of the invention.

BACKGROUND OF THE INVENTION

The development of sensor systems for environmental monitoring is a matter of increasing importance in this country. Environmental contaminants are often present in liquids found in the environment as a consequence of a particular manufacturing process and subsequent discharge of the effluent from the process into sewage systems and waterways. Often times, the discharge contains toxic elements such as lead, silver, mercury, various organic compounds and the like. Heretofore, in order to determine whether or not a given contaminant was present, it was necessary to obtain samples in the field and transport them back to a remote laboratory for analysis by techniques such as gas chromatography, mass spectrometry and the like. This is an inefficient means of testing because of the time wasted in traveling from the field to the laboratory, the necessity of preparing samples for analyses, and so forth. It is also very expensive.

THE PRIOR ART

It is known that elements and compounds can be detected in solution by electrochemical means.

Electrochemical detection means include the use of electrodes connected to instruments such as potentiostats which vary the voltage applied to the electrodes and sense any flow of current through the electrodes. Functionally the electrode potential is varied past the E of a redox couple of interest, i.e., the contaminant, and if a characteristic current flows, the presence of this contaminant in the monitored environment is indicated. By observing the magnitude of the current flow, the concentration of the electroactive specie can be estimated. For qualitative analysis, the specific nature of the unknown element or compound in solution is actually determined by comparing the observed current-voltage (electrochemical) profile with known profiles from a library of responses.

There are several deficiencies inherent in the use of conventional electrodes as detectors. For instance, the selectivity is often poor. That is, the electrode is unable to distinguish between elements or compounds having similar electrochemical profiles because the differences are not sufficiently large to enable precise discrimination to be achieved.

Also, conventionally sized electrodes often have large uncompensated resistance which prohibit their use in solutions of limited conductivity. The rate at which experiments can be performed is likewise limited by high interfacial capacitance. Moreover, conventional macroelectrodes are bulky. In addition, electrode surface fouling often prohibits the reuse of electrodes. For use in environmental/laboratory solutions of variable conductivity, what is needed is a disposable or "throwaway" sensor which may be used only once, then discarded.

Investigators have found that electrochemical detection systems employing ultramicroelectrode arrays (UMA's) have several important advantages over conventional, macro-sized electrodes (i.e., 0.1-100 mm$^2$ in area).

A microelectrode ensemble is described in an article by Penner, et al., in Anal. Chem. 1987, 59, pp. 2625-2630. As stated in the article, the use of UMA's enable higher signal-to-noise ratios to be obtained because under optimum conditions the faradaic signal associated with electrolysis of the analyte is proportional to the geometric area of the UMA, whereas the noise is proportional to only the active elemental area. It is suggested in this article that in order for maximum benefits to be achieved using UMA's with disc shaped elements, the microdiscs should be made as small as possible. In the article are described microelectrodes having disk radii of 1000 and 5000A, and a process for making them which involves electrodeposition of platinum into the pores of a membrane, followed by impregnation with polyethylene, with subsequent removal of the polyethylene and excess platinum. The electrodes made in accordance with the process are made of only one element, that being platinum.

Another article by S. G. Weber in Anal. Chem., 1989, 61. pp. 295-302, states that array electrodes are more sensitive than a solid electrode with the same geometric electrode area. This enhanced sensitivity is stated to arise from the diffusive or hydrodynamic transport of electroactive material from regions of the array surface that are insulating to regions that are electroactive. Thus, detection limits are lowered with the use of microelectrodes.

D. K. Cope and D. E. Tallman (J. Electroanal. Chem., 188. pp. 21-31 (1985), and 205. pp. 101-123 (1986) have shown that an array of microelectrodes in flowing streams, results in signal (current) enhancement and improved limits of detection, relative to conventional macroelectrodes.

M. Otto and J. D. R. Thomas, Anal. Chem., 57, 2647-2651 (1985) have used a collection of macro-sized commercial and in-house fabricated ion-selective electrodes in conjunction with chemometrics to analyze for ions in simulated body fluids. These ion-selective electrodes are only partially specific. Work of this nature has been extended by others, i.e., K. Beebe, D. Uerz, J. Sandifer, and B. Kowalski, Anal. Chem., 60, 66-71 (1988); K. Beebe and B. Kowalski, ibid, 2273-2278 (1988); W. E. van der Linden, M. Bos and A. Bos, Analytical Proceedings, 26, 329-331, (1989).

Part of the work described in these references is aimed toward using relatively non-specific arrays. This is one aspect in common with the invention described herein. However, the techniques are different. Thus, the inventors herein use solid or polymer modified metals and voltammetric, as well as amperometric methods; the references describe strictly potentiometric systems based upon potentials developed across membranes; the methods of detector fabrication are different; the concepts are different; the exact methods of chemometrics used differ; and the overall system design, electronics, software, etc. are very different; the form of use is also very different (i.e., potentially throw-away selective detector based upon relatively non-selective elements).

There are in addition certain deficiencies associated with the microelectrode arrays of the prior art.

Even if they were to be used as electrochemical sensors, being of single material they are not always sufficiently selective to distinguish between elements in solution having similar electrochemical profiles.

Secondly, they were not produced to maximize sensitivity in sensor applications.

Thirdly, in producing these the investigators were pursuing basic research goals. Therefore, they were not concerned with issues confronting field sensor applications, which include the development of methods of inexpensively and reproducibly fabricating sensors for potential "throw-away" applications.

An accurate and economical means of detecting on site the presence of toxic elements or compounds in solutions found in the environment would be extremely desirable. Such preliminary identification of site contamination would justify the need for a more thorough laboratory examination. This provides one motivation for the present invention. In addition, such electrochemical sensors/detectors are needed for use either stand-alone or in conjunction with other analytical methods (i.e., chromatography) in the analysis of samples in the laboratory.

SUMMARY OF THE INVENTION

It is an object of this invention to provide a multielement, microelectrode array-based detection system for analyzing samples in solutions and in natural environments.

It is a further objective of this invention to provide a portable, hand-held detector system, complete with a microcomputer, potentiostat, data acquisition board, other associated electronics and a disposable microelectrode array detector/sensor. Custom software is provided with this system.

It is a still further object of this invention to provide a method of fabricating the disposable multielement, microelectrode array forming a part of the complete hand-held electrochemical sensor system referred to above.

It is a still further object of the invention to provide a multielement, microelectrode array, electrochemical detector to detect the presence of elements and chemical compounds in solution and in the natural environment.

It is yet another object of the invention to provide a multielement, microelectrode array, electrochemical detector having a high signal to noise ratio and improved selectivity.

It is yet another object of this invention to provide a method of detecting and measuring the concentrations of electroactive substances in the environment.

Other objects and advantages of the invention will be apparent from the description to follow, and from the drawings in which:

The microelectrode based detector system of this invention comprises a photolithographically produced multielement, microelectrode array, fabricated on an insulating wafer, preferably, silicon or ceramic, electronically connected to a data acquisition board and a computer having a readout mode, which by means of appropriate software converts signals from the microelectrodes into values indicating the specific types and amounts of electroactive elements or compounds present in a given solution or in the tested environment.

The multielement, microelectrode array, electrochemical detector has a high signal-to-noise ratio and improved selectivity. It is fabricated by placing several different electrode materials on a single insulating wafer to form a plurality of microelectrodes, i.e., an array.

In another embodiment, this invention comprises a method of making the multielement, microelectrode array, and integrating it with appropriate electronics, computational systems, and pattern recognition for data analysis to form a compact, hand-held sensing system.

In still another embodiment this invention encompasses a method of detecting and measuring electroactive elements or compounds in solutions or in natural environments.

DETAILED DESCRIPTION OF THE INVENTION

Figure 1:
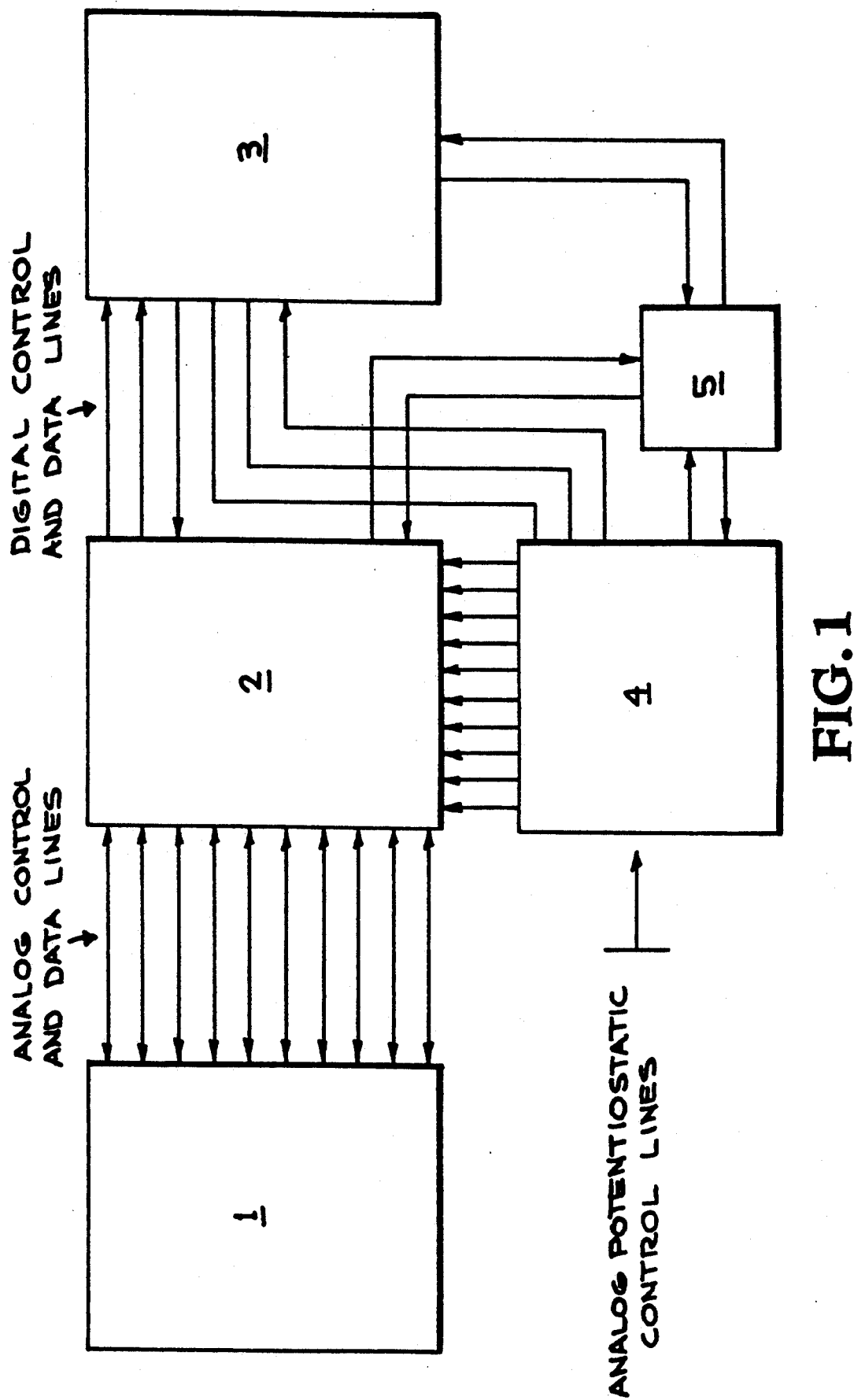
FIG. 1 is a schematic block diagram of the components of the system of the invention.

The complete electrochemical sensor system of the invention is shown schematically in FIG. 1. Block number 1 represents a multielement, microelectrode array electrochemical detector which is normally immersed in a solution for purposes of detection of electroactive elements or compounds. The microelectrode detector is connected by appropriate analog control and data lines to block number 2, which represents data acquisition instrumentation, i.e., amplifiers, multiplexers, and other electronic components. Block number 2 is in turn connected by digital control and data lines to block number 3, which represents a pre-programmed microcomputer which controls the experimental parameters and sequencing, and provides data storage. Block number 4 represents potentiostat circuitry which is functionally the part of the device which controls the electrochemical experiments at the microelectrode array. The potentiostat receives analog control input from block number 1 via block number 2, and is connected by appropriate leads to block number 3. Potentiostatic control is provided to each microelectrode array segment independently. Block number 4 is in turn connected by appropriate leads to block number 5, which represents a system clock and control. This block in turn is connected by appropriate leads to blocks numbers 2 and 3.

Figure 9:
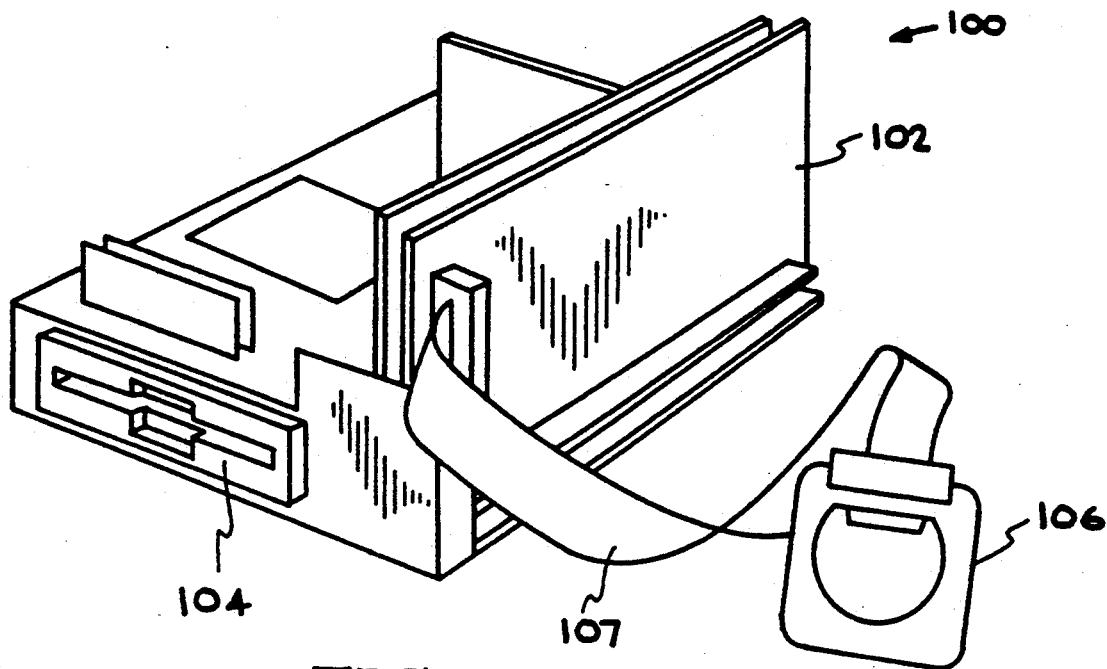
FIG. 9 is a perspective view of the system of the invention with the cover removed from a portion thereof.
Figure 10:
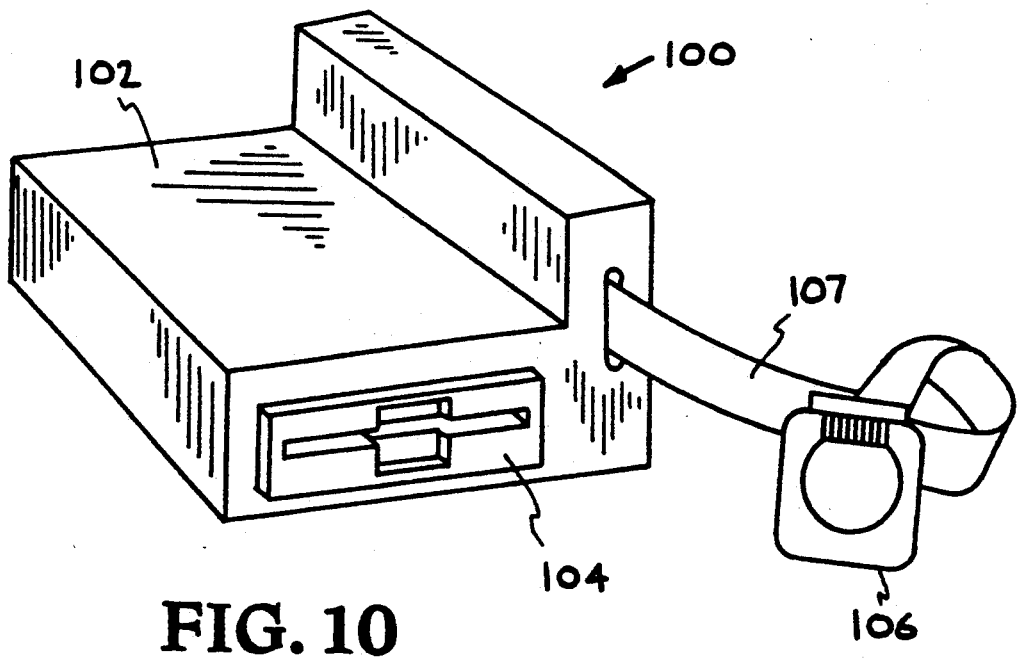
FIG. 10 is a perspective view of the system of the invention with the cover intact.
Figure 11A:
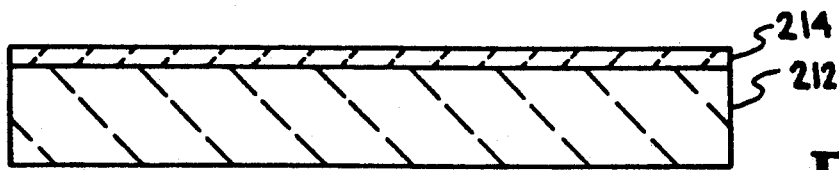
FIGS. 11(a-f) are diagrams of an alternate photolithographic fabrication sequence of a microelectrode array detector.
Figure 11B:
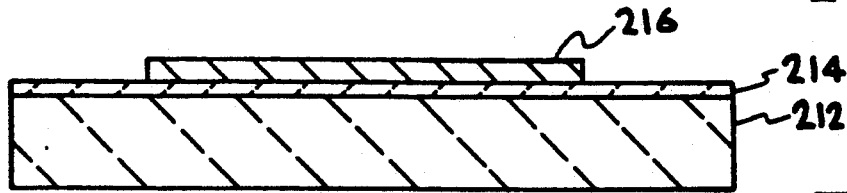
Figure 11C:
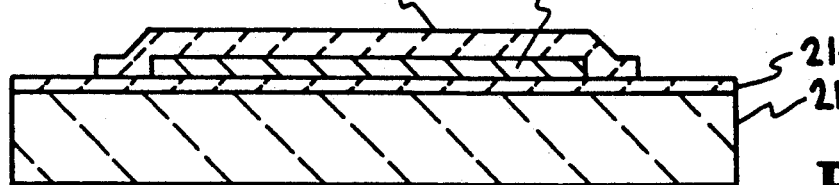
Figure 11D:
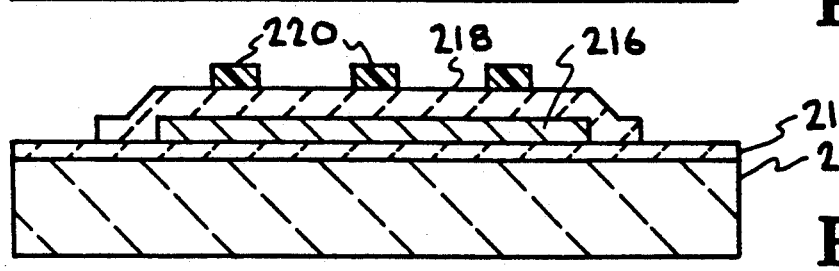
Figure 11E:
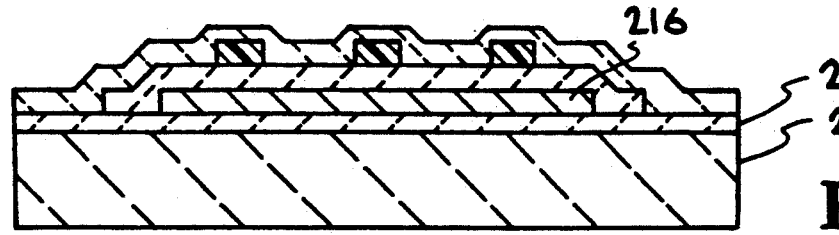
Figure 11F:
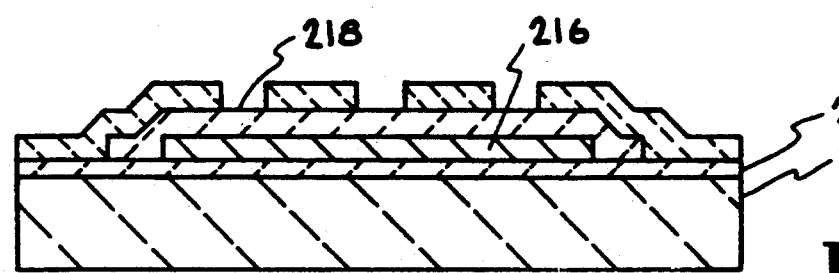

At the electronic heart of the apparatus or system of this invention is a limited function low-powered multiple electrode potentiostat and data manipulation capabilities. As seen in FIGS. 9 and 10, the system 100 consists of two parts: the main electronic control chassis 102 which contains a data acquisition board, potentiostat, and microcomputer having a floppy disk 104, and a sensor/sample chamber 106 connected by a 25 pin shielded ribbon cable 107. In the preferred embodiment the control chassis 102 is approximately $11 \times 10 \times 5$ inches and the sample/sensor chamber 106 is $2.25 \times 2.25 \times 1$ inches. These dimensions do not include an optional keyboard used for programming or a video monitor. Future reductions in size of the various components will enable still smaller units to be built.

The system 100 is equipped to do cyclic voltammetry at various scan rates, ranging from 2.5 mV/s to a maximum of 200 mV/s. It will scan up to 8 different microelectrode array segments (each potentially a different material) which are on the detector substrate. It will automatically change the experimental parameters (i.e., scan rate, direction, range) of the system according to which microelectrode array segment is selected, by means of a software electrode scan table.

Figure 2:
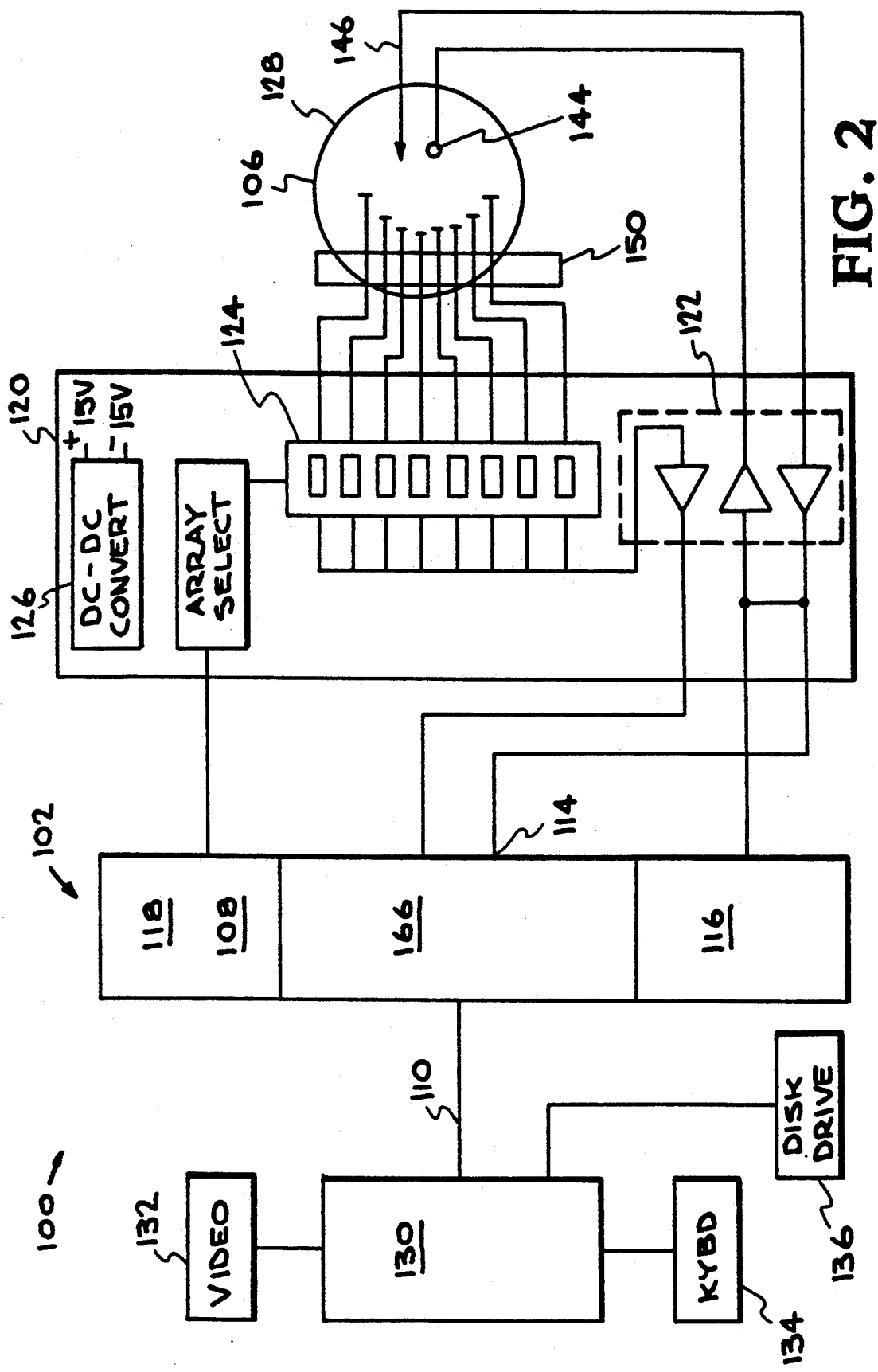
FIG. 2 is a block diagram of the electronic components of the system of the invention.

Referring to FIG. 2, the main component of the data acquistion and control system 102 is a Data Translation, Model 2801/5716 board 108 obtained from Data Translation Corp., Marlboro, Mass. It is a full size plug in card for an IBM PC/AT bus 110. It has a 16 bit analog/digital (A/D) converter 112 with eight input channels 114, two 12 bit digital/analog (D/A) channels 116, and 16 digital input/output (I/O) control lines 118.

A sensor interface card 120 contains potentiostat circuitry 122, a nine channel relay multiplexer 124 with control logic and a low noise 5 V dc to $+/-15$ V dc converter 126. The sensor interface card 120 was designed to fit into a PC/AT computer, and plugs into the PC/AT bus 110. It receives 5 V dc from the bus 110 and consumes approximately 200 mA. This board (card) was designed and fabricated at Lawrence Livermore National Laboratory. Functionally, it is positioned between the data acquisition board 102 and a multielement, microelectrode array 128 positioned in the chamber 106. All signals to the array 128 first are buffered on this board.

The operation of the potentiostat 122 is controlled by a computer 130 and the operating software with no provisions made for manual operation. The computer 130 is connected to the PC bus 110. There are no front panel controls or indicators available for operator intervention. When used in the operator present mode, a video monitor 132 and keyboard 134 connected to the computer 130 provides the operator interface. The computer has a disk drive 136 connected to it.

The compact detector system 100 is based on the Intel 286 chip set although any other comparable chip can be used. An Ampro Corp., Little Board/286, sold by Ampro Corp., Sunnyvale, Calif., was chosen as the specific platform to provide the computing and control logic. It is a single board PC/AT equivalent computer system, and measures $5 \times 8 \times 0.75$ inches tall. The computer system is based on CMOS logic and has low power consumption. Fully equipped, it will draw approximately eight watts at 5 V dc.

The Ampro computer system operates under DR-DOS (Digital Research - DOS), which is compatible with MS-DOS (Microsoft-DOS) and application programs which run under MS-DOS. An advantage to using DR-DOS is its support of disk-less operation, using eeproms (electrically erasable programmable read only memory), solid state disks and other non-volatile silicon memory devices. In the device used in the system of this invention, a 1.44 Mbyte floppy disk drive is used. The floppy disk storage can be replaced with solid state memory which will in turn decrease both the system size and more importantly, the power required for battery operation.

The software for the system was written using Microsoft Quick C, sold by Microsoft Corp., Seattle, Wash. It is a relatively fast and concise language. It can also be written on a PC/AT platform, and is fully supported by DR DOS. In addition, the software drivers for the data acquisition system 102 (daq) were available in Microsoft C. This allows the freedom to use pre-written function calls rather than writing personalized assembly language code for the board operation.

Appropriate software can be written by those skilled in the art. A number of companies provide software for use with larger laboratory electrochemistry equipment. A suitable commercially available program is Model 273 Electrochemistry Software, sold by the Princeton Applied Research Corp., Princeton, N.J.

Other suitable software programs are sold by Bioanalytical Systems, Inc., West Lafayette, Ind. and are dedicated for use with their laboratory electrochemistry system, the BAS 100A. Cyclic and Square Wave Voltammetry Software compatible with the IBM PC can be obtained from Covalent Associates, Woburn, Mass.

Figure 3:
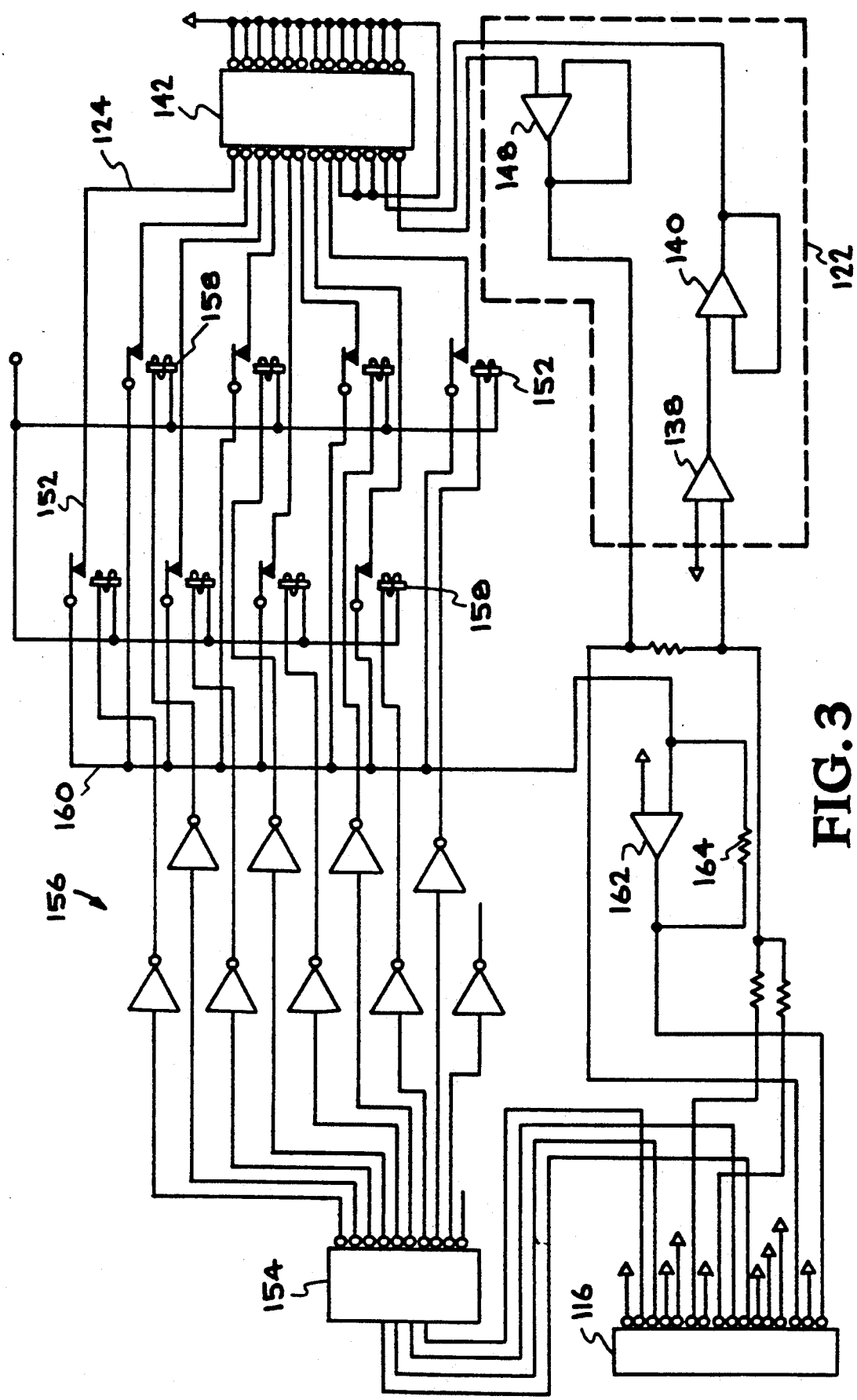
FIG. 3 is a detailed circuit diagram of a portion of the electronic circuit of the detector system of the invention.

Referring to FIGS. 2 and 3, the voltage ramp from the digital to analog converter channel 116 is summed in a summing amplifier 138, along with the feedback from a reference electrode, which is located either in the multielement microelectrode array 128 or external to it. The sum of these signals is then passed to a current amplifier 140 which has a unity voltage gain. The output of the current amplifier 140 is then fed to a connector 142, and on to the auxiliary electrode 144 of the array 128. The return signal from the reference electrode 146 is sent from the array 128 back to connector 142 and then to a unity voltage gain amplifier 148. The output of this amplifier is sent to the summing amplifier 138 and to channel 1 of the daq board 102. This output provides the applied cell voltage. This data is stored and used for the post-run graphic plots (x axis).

The signals from the sensor electrode arrays 128 are directly cabled to a sensor housing connector 150. The working electrode (w.e.) signals (these are the individual microelectrode array segments) are brought onto the interface card 120 through connector 142 and each of the w.e. signals is brought to a separate input relay (K1-K9) 152. The control signals which are used to select the desired electrode array are digital output channels 0-3 from converter 112. The desired relay K1-K9 is selected by software and the correct value is output to the sixteen line to one decoder 154. There can only be one relay energized at one time. The output of the decoder 154 drives current buffers 156 which in turn energize the selected relay coil 158.

When a relay 152, etc. is energized, the normally open contact of the relay is closed and the selected electrode output is connected to the relay common terminal 160. The common terminal 160 of each relay 152 is connected in parallel to the I/V amplifier 162. This amplifier has an output signal that is equal to the selected electrode output current times the gain resistor 164. There is only one gain resistor shown, but modifications will allow for several software selectable gains, which will allow for a greater sensitivity range. The output of the I/V amplifier 162 is sent to the input channel A/D 166 (1 of 16) of the daq 102 and is stored as a representative value for the current flow.

All values which are used in the test run, where the microelectrode array segments are sequentially accessed, are set as default values during pre-run. By incorporating default values, stand-alone operation is possible. This can be used when continuous or repetitive remote site monitoring is required. If a keyboard error occurs during the initial booting of the system, the computer 130 assumes that the system is in the stand-alone mode and the operator information exchange routines are removed. The operator information exchange routines preview the scan parameters showing the operator the default values prior to actual operation and offer the means to modify the scan parameters.

To program the sensor system 100 for automatic operation, the following information is required:

1. Sample identification number (seven or less characters).

2. Electrode array scan sequence table (1-8, any order).

Contains the following information for each electrode:
A. Scan potentials (Initial, Vertex 1, Vertex 2).
B Scan speed (volts/sec).
C. Number of scan cycles required (1-5).
D. Data averaging required (Y/N; if yes (1-5)).
E. Quiet time (sec).

Upon completion of the parameter input section, the system 100 initiates a voltage scan using an internally generated software trigger. The first scan is taken using a dummy cell with a 100 Kohm resistor to establish linearity and offset of the potentiostat circuitry. When this scan is complete, the relay corresponding to the first electrode scan table entry is energized and the scan commences.

Measurements are made at every discrete step of the D/A channel 116, which is usually set to 2.5 mV, the minimum step allowable, although larger voltage steps can be used. The step period is adjusted using a timing loop. With an adjustable loop counter the scan speed can be changed. When a measurement is made the result, i.e., current flowing through the cell, is stored in an array with the corresponding applied cell voltage. At the conclusion of the scan, the array is written to a file stored on the floppy disk. The software automatically appends a run suffix letter to each of the resulting scans, thus allowing for post run identification of the different scans.

Figure 4:
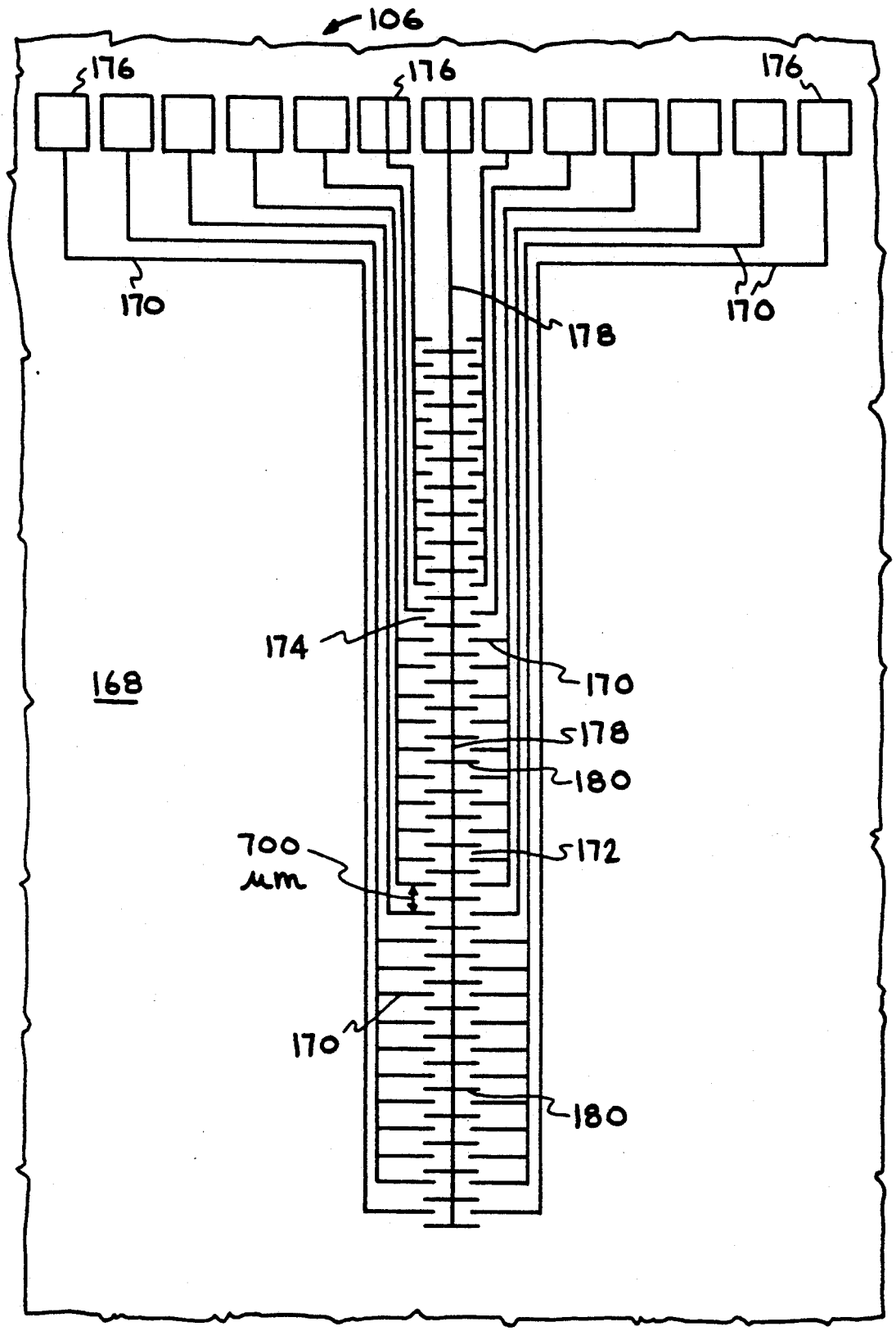
FIG. 4 is a diagram in plan view of a multielement, microelectrode array detector.

One embodiment of the multielement, microelectrode electrochemical detector of the invention is shown in FIG. 4. The detector 106 comprises a flat wafer 168 which contains deposited thereon a plurality of parallel electrodes 170 projecting inwardly into a longitudinally extending core area 172. Each of the electrodes 170 is individually insulated from the others by a silicon or ceramic matrix 174, and is connected at the top to a connector pad 176. Several individual microelectrodes can be connected together to form a segment. The electrodes in the array are divided into segments and can be made of the same or different materials. However, in order to function with selectivity, the array must contain at least two different electrode materials. Electrodes can be made from platinum, gold, carbon, vanadium, iridium, and the like.

Centrally located in the core area 172 of the microelectrode array 106 is a platinum counter/reference electrode 178 which has transversely situated leads 180 located at various points. The leads 180 are situated approximately equidistant between the electrodes 170 projecting from the periphery of the core area 172 into the center thereof. Thus is provided a multielement array of microelectrodes in close proximity to each other, but insulated from each other by suitable means.

In the embodiment shown in FIG. 4, the length of the core area 172 is approximately 2.54 centimeters, and the width of the connecting pad 176 array is approximately 2.03 centimeters. The number of electrodes 170 or the number of different types of materials that can be present is limited only by the availability of physical methods for deposition and the resolution of the microlithographic technique.

The platinum electrode 178 running down the center of the core area 172 has a potentially versatile role. It can function as the auxiliary electrode in a "2-electrode" experiment; a counter electrode alone with separate reference; or even as the reference electrode. When functioning as the latter it can be used as a "bare" platinum metal in the "pseudo-reference" mode. Preferably, the surface of this electrode is covered with a polymer which incorporates redox centers which obey the Nernst relation and which "pin" the potential of this electrode.

Contact to the electrodes 170 and 178 is made on the pads 176 at the top of the array 106. There are two pads 176 for each array electrode material. One pad is connected to a single microelectrode to determine individual responses, and the other is connected to a segment of 10, which increases the sensitivity through additive responses. There are two pads shown for each electrode material. From left to right in FIG. 4 the electrode materials are: Pt (pads 1 and 2), carbon (pads 3 and 4), V (pads 5 and 6), Pt auxiliary (pad 7), Au (pads 8 and 9), Ir (pads 10 and 11), and Pt (pads 12 and 13). Thus, as described in Example 1 below, and shown in FIG. 4, six different electrode materials can be used. Preferably, the width of each working electrode 170 is 5 microns, while that of the center platinum counter/reference electrode 178 is 10 microns. As described in greater detail below, a mask of photo-resist or silicon dioxide is deposited over the array following deposition of the last material. This final step masks the electrical lead lines and exposes only the tip (last 20 micrometers) of each electrode 170. Defined in this manner, each individual microelectrode 170 has an area of 104.5 square micrometers exposed for environmental monitoring.

In a preferred embodiment, the transversely oriented arms 180 of the electrode 178 running down the center of the core area 172 of the array is distanced approximately 350 micrometers from the inwardly projecting tips of the electrodes 170 previously described.

Figure 5:
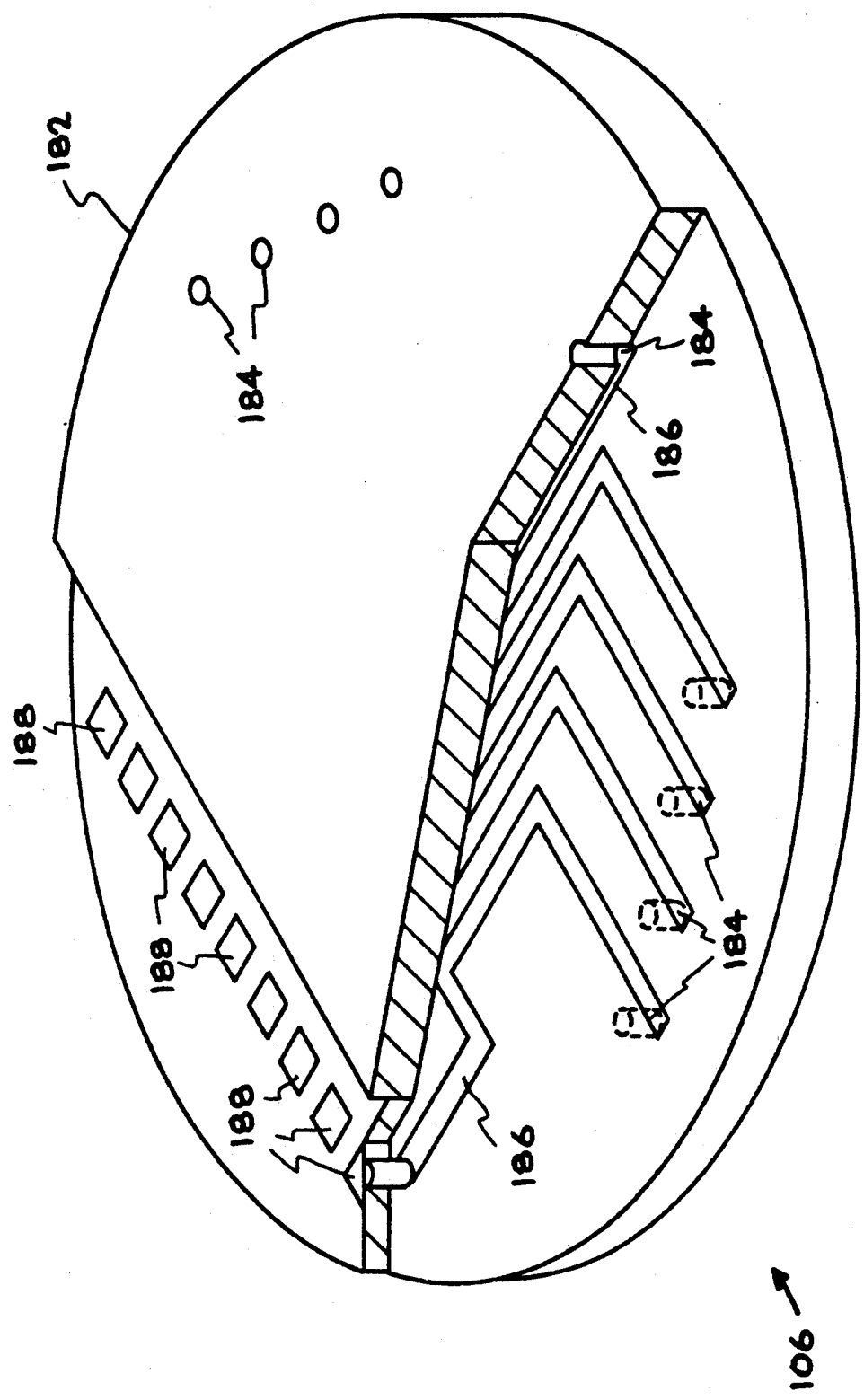
FIG. 5 is an alternative embodiment of the multielement, microelectrode array detector of the invention.
Figure 6A:
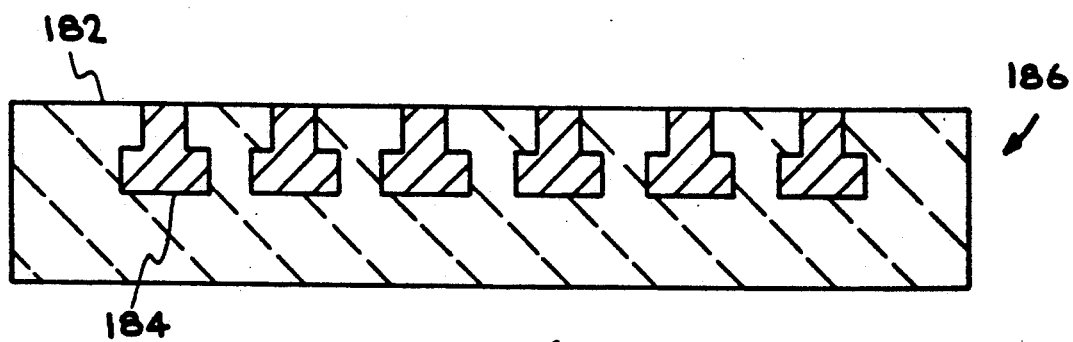
FIGS. 6(a-d) are cross-sectional views of various alternative embodiments of the multielement, microelectrode detector of the invention.
Figure 6B:
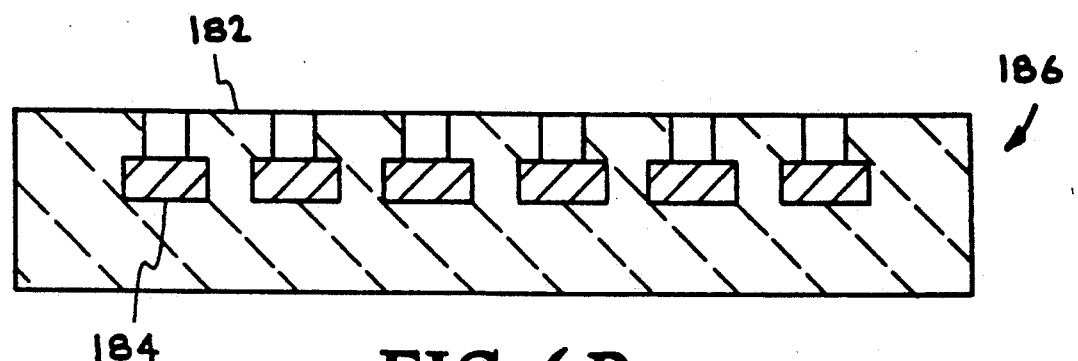
Figure 6C:
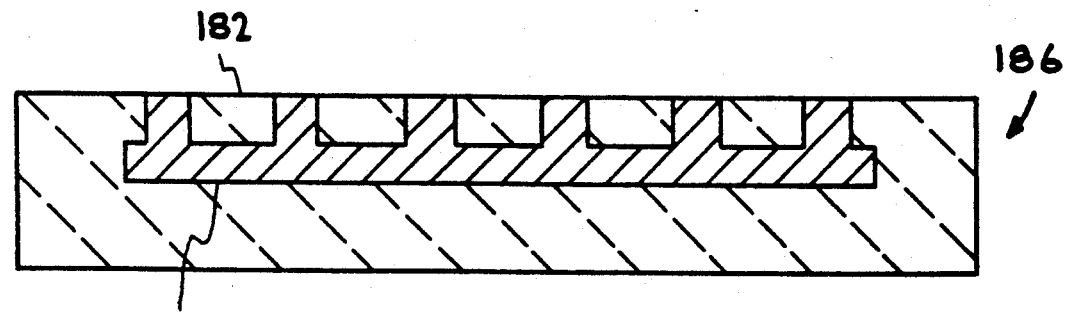
Figure 6D:
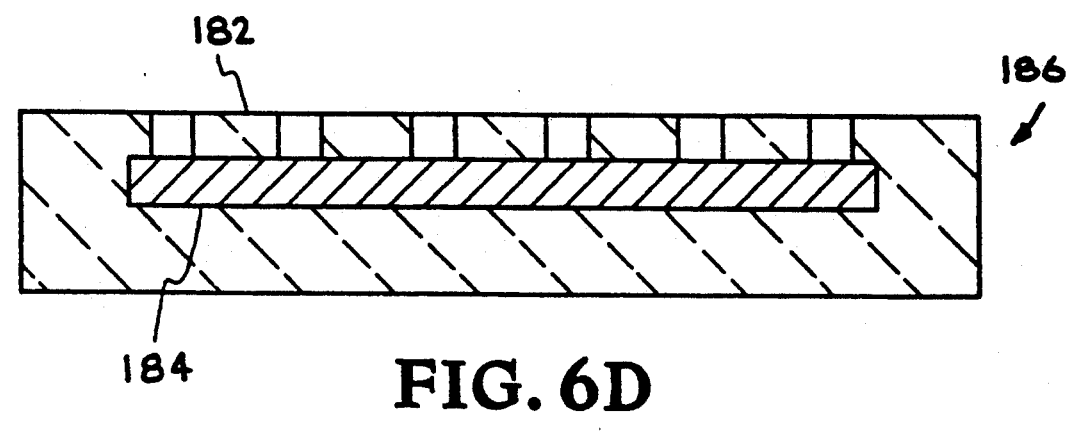
Figure 7A:
FIGS. 7(a-g) are diagrams of the photolithographic fabrication sequence for the array detector of FIGS. 4, 5 and 6.
Figure 7B:
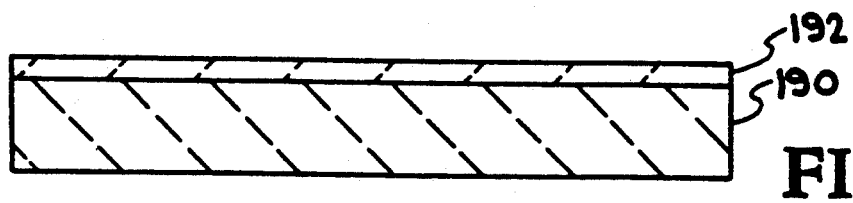
Figure 7C:
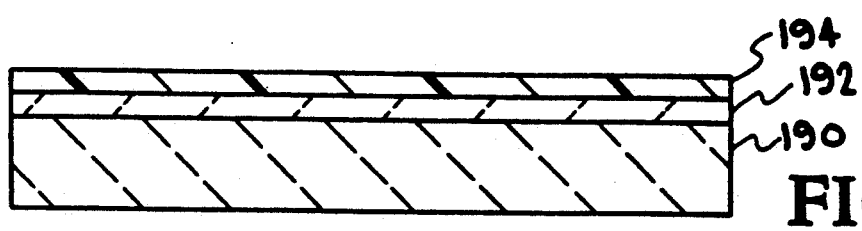
Figure 7D:
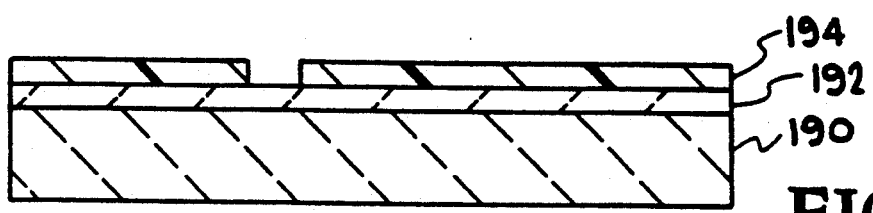
Figure 7E:
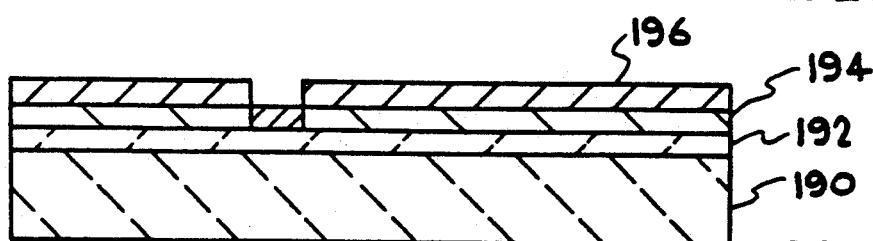
Figure 7F:
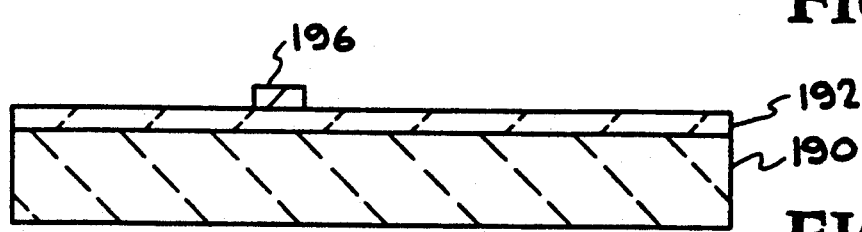
Figure 7G:
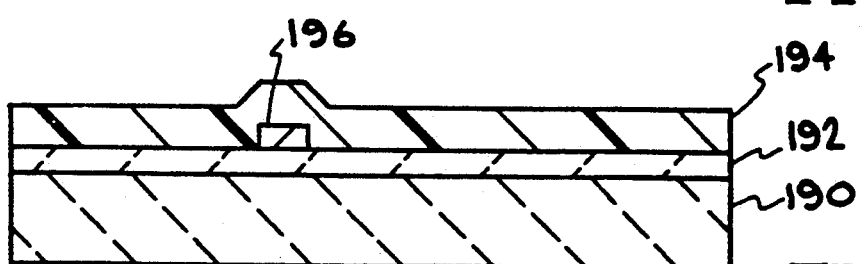

An alternative embodiment of the microelectrode detector of the invention is shown in FIGS. 5 and 6.

In FIG. 5, the detector 106 is shown as a circular wafer 182 which is fabricated from an insulating material, preferably silicon or ceramic. Positioned on the wafer 182 at various locations are microelectrodes 184 which have been vapor deposited on the wafer. The upper surface of each of the microelectrodes 184 is exposed to the environment. Each of the microelectrodes is connected by a lead 186 to a tab 188. The tabs 188 are in turn connected by appropriate analog control and data lines (see FIGS. 2 and 3), to data acquisition instrumentation 102.

FIG. 6 is a cross-sectional view of various embodiments of the detector of the invention. As can be seen, the tips or ends of the microelectrodes are exposed to the ambient environment. Either individual microelectrodes can be used, or, in the preferred embodiment, several can be connected together to form an array. Also, the electrode surface can either be Planar with the insulator surface (FIG. 6(a) and (c)), or it can be recessed in a well (FIG. 6(b) and (d)).

Figure 12:
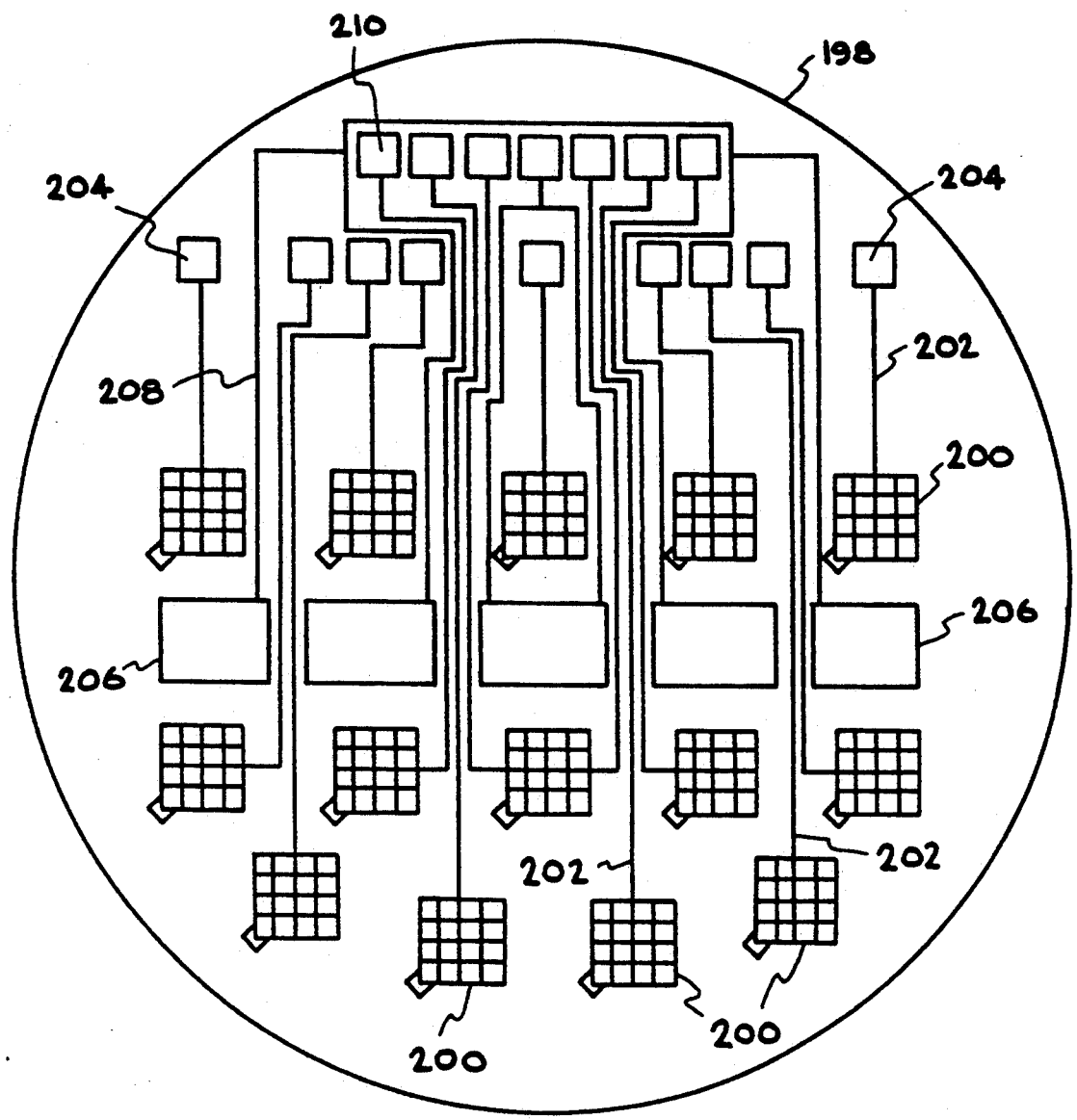
FIG. 12 is a diagram in plan view of an alternate embodiment of the microelectrode array detector of the invention.

A particularly preferred embodiment of the array detector 106 of the invention is shown in FIG. 12. As shown, the detector 106, comprises a circular wafer 198 which is fabricated from silicon, ceramic, or other insulating material. Positioned on the disc 198, at predetermined locations are microelectrode arrays in the form of blocks 200 which have been vapor deposited in the manner previously described. Each block 200 is connected by appropriate leads 202 to the electrical contact tabs 204 positioned at the top of the wafer 198.

Also positioned on the wafer 198 are somewhat larger array blocks 206 which are connected by leads 208 to other tabs 210. The larger blocks 206, which are all interconnected, are solid metal surfaces and are used as an auxiliary electrode, not sensing elements. All of the lead lines, 202, are unexposed to the environment.

This device (FIG. 12) can contain up to one million active sensing electrodes and 14 different electrode materials. Each 4×4 mm block 200 is actually an array of 77,000 microelectrodes, each of which is a disc 5 $\mu$m in diameter separated from an adjacent disc by 14.5 $\mu$m. The individual microelectrodes in each block are interconnected, as in FIG. 6(d). A temperature measuring device (RTD), pH measurement, and possibly even a humidity sensor can be incorporated onto a single wafer like this along with the sensor microelectrode arrays. On particular initial arrays, the electrode materials are Pt, Ti, Ni, Cu, Al, and Au, Ag, and Ir, some of which are repeated. Other arrays contain a greater variety of sensor electrode materials. Chemically selective coatings such as Nafion (registered trademark of DuPont, Wilmington, Del.), phthalocyanines and polymers can be deposited onto the bottom four blocks 200. Up to 14 different electrode materials (8 have actually been used) and over 960,000 electrodes, each a disc 5 $\mu$ in diameter, have been prepared on a single substrate.

The procedures described allow for a high degree of versatility in the design of sensors incorporating different electrode materials. The choice of materials depends upon the particular application. The use of the greater number of electrodes, (and smaller size) and greater number of materials leads to enhanced sensitivity and selectivity.

It should be understood by those skilled in the art that the drawings represent various embodiments of the invention, and that other combinations and arrangements of multielement microelectrode arrays, computers, software and the like, can be put together to achieve the desired purpose.

What is essential, is that signals from the microelectrode detector are transmitted to suitable data acquisition instruments and a computer having sufficient computing power, and appropriate software, to analyze these signals, compare them with known signals from various ions and compounds (a library of responses), and make a determination as to the elements present in solution in which the hand-held electrochemical detector is placed.

The microelectrode arrays of this invention are produced photolithographically, using a negative lift-off procedure. A prototype array is shown in FIG. 4. A total of 66 microelectrodes selected from the materials above were fabricated on each silicon substrate (standard 2" wafers of 12 mil thickness). The individual materials are deposited sequentially in precise geometric registry. An outline of the overall procedure is given in FIG. 7 and is described below. This procedure was used to fabricate the earlier arrays shown in FIG. 4.

1) In all cases, standard 2" diameter silicon wafers 190, (100) orientation, which are 12 mils in thickness were used.

2) In the first step, in order to create a highly insulating substrate, a 1500 A layer of silicon nitride 192 is deposited onto the wafer using low pressure chemical vapor deposition. This layer is then subjected to a plasma etch in oxygen at 300 watts for 20 minutes, and then the chip is allowed to cool.

3) A layer 194 of photo-resist (AZ 1350J) is spun onto the wafer at 4000 rpm. This takes approximately 25 seconds and results in a layer 1.25 $\mu$m in thickness. The photo-resist layer is then subjected to a soft bake at 85° C. for 25 minutes and then allowed to cool.

4) The patterns for subsequent metal deposition are then generated. This is accomplished by first overlaying masks on the wafer and then exposing the wafer to UV irradiation (405 nm) using a power density of 148 mJ/cm$^2$. There are then 5 steps preceding metal deposition. These are: i) soak in chlorobenzene for 5 minutes at room temperature, then blow dry; ii) spray develop for 1 to 1.5 minutes at 300 rpm to dissolve the photo-resist which has been exposed to UV; iii) spray rinse with deionized water at 500 rpm for 30 s to remove the developer; iv) spin dry the wafer at 3000 rpm for 30 s; and finally, f) plasma etch the wafer at 100 watts power in N$_2$ for 5 minutes, followed by treatment in O$_2$ for 3 minutes.

5) A thin layer of niobium (100 A) is deposited in order to increase adhesion of the sensor materials. The first electrode material 196 is then deposited by electron-beam evaporation. In each case, the thickness of material was 0.1 $\mu$m.

6) Unwanted metal is lifted off the wafer with acetone (which actually removes the photo-resist 194 underlying the unwanted metal), leaving the desired electrode 196 in place.

7) Steps 3-6 are now repeated in order to sequentially deposit the rest of the sensor materials with accurate registry between the metal patterns.

In a final step (not shown) once all the microelectrode arrays have been deposited, a layer of SiO2 is then deposited through a mask so that all lead lines are masked and the exact microelectrode areas to be exposed to solution are defined. Besides SiO2, other masking agents such as a photo-resist are also possible. Following the photolithographic fabrication procedure, the array is rinsed with deionized water, then acetone, and finally absolute ethanol, then allowed to dry prior to use.

This invention will be more fully understood by reference to the following examples, which are intended to be representative of the invention, but not limiting thereof. The invention is limited only by the claims appended hereto.

EXAMPLE 1

For a given application, the choice of electrode materials will depend upon several electrochemical and materials considerations. In one example, the voltammetric properties of 10 different electrode materials [Ir, Pd, Ag, Cu, Au, Pt, V, AISI 304 stainless steel, C (graphite), and Ti] using electrodes of conventional size (about 0.1 cm$^2$ in area) were first evaluated. From these measurements a set of 5 different materials was selected for incorporation into the microelectrode array device shown in FIG. 4. Criteria for materials selection included: voltammetric range, stability, varied response to compounds of interest, reproducibility, and ease of fabrication (using photolithography). The materials selected for the prototype microelectrode array detectors were Pt, Au, V, Ir, and carbon.

A series of tests were performed to show the utility of the multielement array approach to sensor design and to show that chemometric theory (in this case, information theory) could be useful in the selection of sensor materials. This particular study focused on the microelectrode array detector alone, rather than the electronics or complete system displayed in FIG. 10. Later studies utilize the complete compact sensor instrumentation described herein.

The compounds used in this example are listed in Table 1. The first set consisted of explosives; while the second set included structurally similar non-explosives. Where commercially available, all chemicals used were of analytical reagent quality. The explosive compounds, TNT, RDX, HMX, and PETN were of commercial quality (approximately 98% purity). The solvent used was dimethylsulfoxide (DMSO), with 0.1 M tetra-n-butylammonium tetrafluoroborate (TBABF$_4$) added as supporting electrolyte. Solutions were made 2.5 mM in each compound studied. The solutions were purged with argon prior to running a cyclic voltammogram. In addition, activated alumina was added just prior to each experiment to absorb as much residual water from solution as possible.

TABLE I: COMPOUNDS

SET 1

2-methyl-1,3,5-trinitrobenzene (TNT)
Octahydro-1,3,5,7-tetranitro-1,3,5,7-tetrazocine (HMX)
Lexahydro-1,3,5-trinitro-1,3,5-triazine (RDX)
2,2-bis[(nitroxy) methyl)]-1,3-propanediol, dinitrate (PETN)

SET 2

4-nitro-o-phenylenediamine
2,4-dinitrophenol
P-nitroaniline
2-nitroresorcinol

A three electrode configuration was used where center Pt electrode served as a counter electrode and a separate saturated calomel reference electrode was used. The reference electrode was used in conjuction with a salt bridge (containing 0.1 M TBABF$_4$ in dimethylsulfoxide) to make contact to the solution. Voltammetric measurements were obtained using each of the different microelectrode materials. All measurements were made using the array of ten microelectrodes for each material as the "working electrode". The arrays were accessed sequentially.

Figure 8:
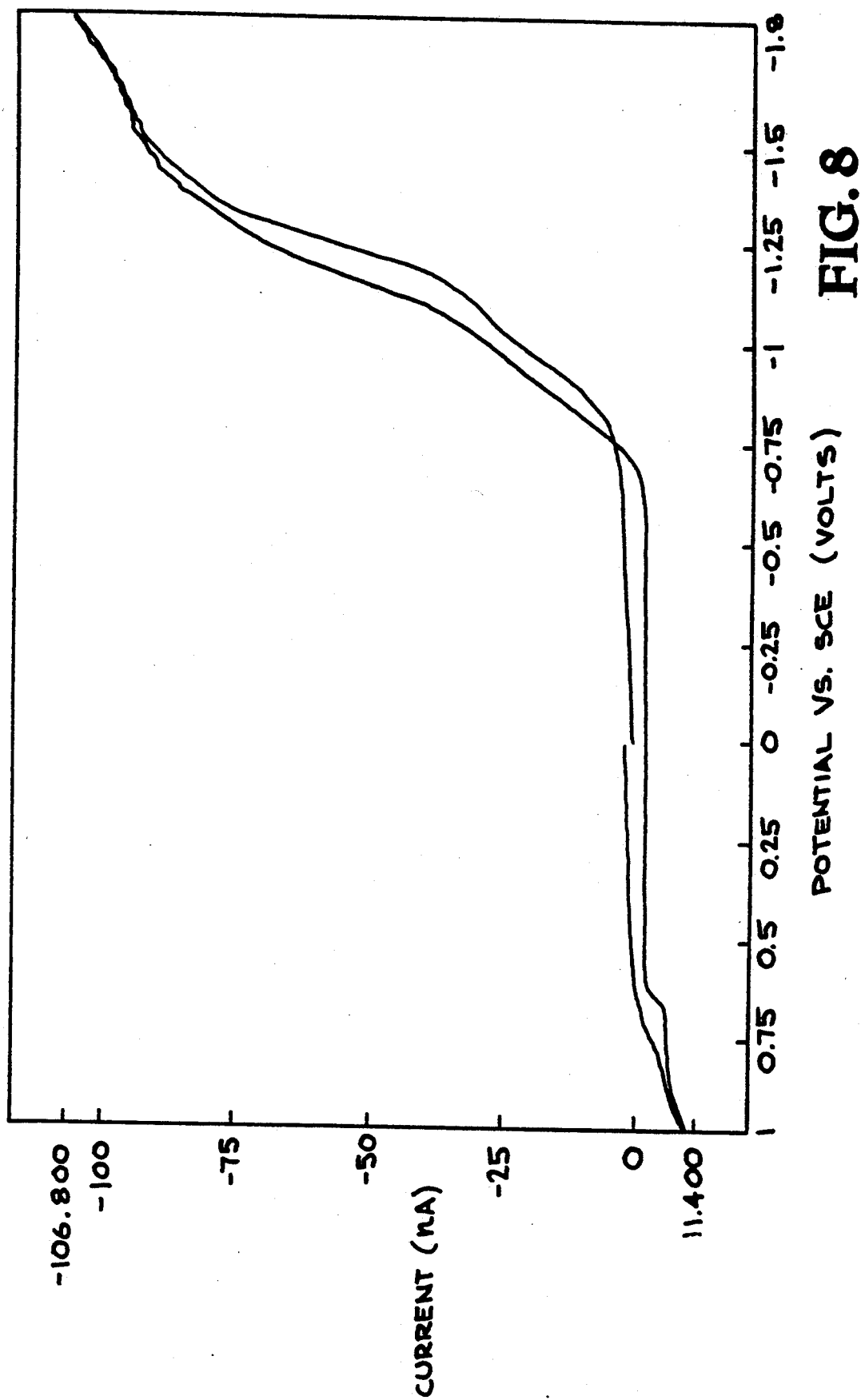
FIG. 8 is a cyclic voltammogram for hexahydro-1,3,5-trinitro-1,3,5-triazine (RDX) at 2.5 mM in dimethylsulfoxide at the Au microelectrode array segment of FIG. 4 (10 microelectrodes connected in parallel).

An example of the response obtained is shown in FIG. 8, which displays the cyclic voltammogram, obtained at the rate of 20 mV/s, for RDX on the Au microelectrode segment (electrical contact made on 6th pad at top from right in FIG. 4).

A number of statistical approaches for the evaluation of chemical data and for the optimization of experimental protocols have been developed within the field of chemometrics, with application to a number of analytical methods. Information theory has been used to quantify the information content of electroanalytical measurements described herein and guide the selection of optimum sets of electrode materials. This theory is discussed in greater detail below, which recounts a study that demonstrates one measurement strategy and is published in Analytical Chemistry, Vol. 62, No. 17, Sep. 1, 1990.

Information content of the data of this example was evaluated using the formalism of information theory developed by Shannon for probabilistic models of communication (Shannon, C. E. Bell System Technical Journal, 1949, 27, 379 and 623). Simply stated, this theory says that the most information is provided by the event least likely to occur spontaneously. This principle is formalized by the concept of entropy which expresses increased information in terms of decreased uncertainty. The quantitative expression for the average information content is given as:

$$H = - \sum_{i=1}^{N} p_i \log_2(p_i) \quad (1)$$

In this equation H is the entropy (or average information), N is the number of events (see below), and $p_i \ldots p_n$ are the probabilities of occurrence for each event in the system under consideration. Therefore, the average information is equal to a weighted average of the specific information, given as $-(\log_2 p_i)$, for each event in the system under consideration. When quantified using this expression, information content is expressed in terms of "bits".

In order to simplify the analysis, tables were prepared which correspond to binary event markers which equate the measurement at a given potential of current exceeding background as the occurrence of an "event", whereas observance of no excess current is equated to the absence of an event. These states can be represented as "1's" and "0's", respectively for each potential considered in the analysis. Thus, the occurrence of a "0" in the data array would correspond to an observation of only capacitative or impurity currents at a given potential. The occurrence of a "1" would correspond to the observation of currents exceeding the detection limit (+3 std, dev. units) at a given potential. (Refer to Tables II and III below for typical data arrays).

The guidelines applied here for constructing a data array for information theory analysis were as follows:

1) Examine voltammetric currents at 0.1 V intervals.

2) Select data from up to 5 information channels (e.g., current at 5 different potentials for a single electrode; or current at one potential for 5 different electrode materials).

3) Platinum was selected as the electrode material for multiple potential sampling; Pt, Au, C, Ir, and V were selected as the electrode materials for the single-potential sampling.

4) Select data channels with the least probability of ambiguity regarding the detection of the presence or absence of the compounds of interest.

5) Select channels providing the least redundant information (i.e., with greatest variety of response patterns).

Therefore, even though full cyclic voltammograms were run on all the compounds, for the purpose of demonstration we evaluated the information content using a single electrode potential ($-1.2$V) for the array of five materials; for the platinum microelectrode array five different potentials were used ($-0.2$, $-0.5$, $-0.8$, $-1.0$, and $-1.2$). In the situation considered here, the same number of measurements were evaluated in each case and the information content can be directly compared. The data collected are summarized in Table II and III. The probabilities of event occurrence was tabulated for each potential (when platinum alone is considered, Table II) or for each electrode material (Table III). Then, the average information content was evaluated using Shannon s formula (Equation 1), where the sum runs over N, the columns in Tables II or III.

TABLE II

TABULATION OF RESULTS OBTAINED USING A SINGLE MATERIAL (PT) MICROELECTRODE ARRAY

| Compound | Current At Pt Microelectrode Array Potential (Volts vs. SCE) | | | | |
|---|---|---|---|---|---|
| | −0.2 | −0.5 | −0.8 | −1.0 | −1.2 |
| 2,4-dinitrophenol | 0 | 1 | 1 | 1 | 1 |
| 2-nitroresorcinol | 0 | 0 | 1 | 1 | 1 |
| 4-nitro-o-phenylenediamine | 0 | 0 | 0 | 0 | 0 |
| p-nitroaniline | 0 | 0 | 0 | 0 | 0 |
| TNT | 0 | 0 | 1 | 1 | 1 |
| HMX | 0 | 0 | 0 | 0 | 0 |
| PETN | 0 | 0 | 0 | 0 | 1 |
| RDX | 0 | 0 | 0 | 0 | 1 |
| $P_i$ | 0 | 0.12 | 0.38 | 0.38 | 0.62 |

TABLE III

TABULATION OF RESULTS OBTAINED USING MULTI-MATERIAL MICROELECTRODE ARRAYS

| Compound | Current at −1.2 V vs SCE at various microelectrode arrays Electrode | | | | |
|---|---|---|---|---|---|
| | Pt | Au | C | Ir | V |
| 2,4-dinitrophenol | 1 | 1 | 1 | 1 | 1 |
| 2-nitroresorcinol | 1 | 1 | 1 | 1 | 0 |
| 4-nitro-o-phenylenediamine | 0 | 0 | 0 | 0 | 0 |
| p-nitroaniline | 0 | 0 | 0 | 0 | 0 |
| TNT | 1 | 1 | 1 | 1 | 0 |
| HMX | 0 | 0 | 0 | 0 | 0 |
| PETN | 0 | 1 | 0 | 1 | 0 |
| RDX | 1 | 1 | 0 | 0 | 0 |
| $P_i$ | 0.50 | 0.62 | 0.38 | 0.50 | 0.12 |

For our experimental parameters, it was found that the average information content of out measurements using the single microelectrode material (Pt) and five different analysis potentials was 1.86 bits; while the average information content using the full matrix detector with five different microelectrode materials and a single analysis potential ($-1.2$V) was 2.32 bitsw. This simple analysis provides a quantitative figure of merit which clearly indicates enhanced information content using the multielement, microelectrode array approach (by 25% in this case). Other comparisons yield an information content comparison enhancement of up to 47% (see previously referenced publication). The enhanced information content using the multielement array approach results in better selectivity for these sensors.

One can apply numerous chemometric methods to analyze the data received from the multielement array detectors of this invention.

In addition to the foregoing analyses by Shannon's information theory, other techniques include pattern recognition methods using artificial neural networks, such are described by R. P. Lippmann, IEEE ASSP Magazine, pp. 4-22 (1987).

Such artificial neural networks have been used to examine pesticide effluents with the array of FIG. 4. They have also be used to analyze unknown solutions containing heavy cations such as $Pb^{+2}$, $As^{+5}$, $Cd^{+2}$, $Mg^{+2}$, and $Cr^{+6}$.

The following example illustrates a method of manufacturing an embodiment of the multielement, microelectrode detectors of this invention (See FIGS. 11 and 12).

EXAMPLE 2

A ceramic wafer two inches in diameter and 10 mil thick, is obtained which has been coated with a 100 A thick layer of chromium, then a layer of gold. The gold has a depth of approximately four micrometers. The gold serves as a conducting path on top of the insulating ceramic. The purpose of the chromium is to act as an adhesive between the ceramic wafer and the gold.

The gold coated wafer is coated with a ¾ to 1 micron thick positive photo-resist solution (American Hoest AZ 1350J). A photo-mask containing the desired circuit pattern is then contacted to the wafer, and the photo-resist coating on the wafer is exposed to ultraviolet light. The ultraviolet exposed photo-resist can be dissolved with a developer, exposing the gold. The gold is then etched away in those areas not protected by the photo-resist, leaving the desired circuit pattern in gold intact. Thereafter, the remaining photo-resist is dissolved away in acetone.

After the photo-resist is removed, a desired sensor material or materials is applied to selective portions of the gold circuit.

This is accomplished with the use of a shadow mask which is applied over the gold circuit pattern. The shadow mask is a silicon wafer which has 4×4 mm holes matching the sensor pad outline in it at predetermined locations. With the shadow mask in place, the desired sensor material is vapor deposited over the mask. The sensor material penetrates the hole, and is deposited directly on the predetermined portions of the gold circuit. This step is repeated, i.e., sensor deposition, using shadow masks with different patterns, for as many different sensor materials as it is desired to put on a single wafer. A platinum electrode is formed in the center of the wafer by depositing a platinum metal through the shadow mask. The platinum electrode can be used as a reference or auxiliary electrode. Other sensor materials which can be used include for example, Cu, Ag, Cr, Va, Ir, C, Ti and Ni. The sensor materials are normally applied to a thickness of approximately 0.5–1.0 μm.

Next, a negative photo-resist, Kodak Negative Resist Type 747, is applied to the surface of the wafer. After the photo-resist is applied, another photo-mask having a number of opaque dots on the surface corresponding to the locations of the previously applied sensor material, is placed over the alumina-ceramic wafer and exposed. The negative photo-resist polymerizes in those areas exposed to ultraviolet light.

Thereafter, the photo-resist coated wafer is placed in a developer which dissolves away those areas not exposed, i.e., the areas underneath the dots in the photo-mask.

Thus, the sensor material underneath the dots in the photo-mask is exposed to the environment, or liquid to be sampled as the case be be. The only exposure of the liquid to be sampled comes through those dot shaped sensors which are exposed. The dimensions and spacings of the microelectrode sensors can be varied; but in one example corresponding to FIG. 12, they were made to be 5 μm in diameter separated by 14.5 μm center-to-center.

The potentially disposable multielement microelectrode detector system of this invention is a new and unique approach to electrochemical analysis of samples. While the potentially disposable detector system and hand-held detector which forms a part thereof was developed for the purpose of sampling in the natural environment, it should be realized by those skilled in the art that it can also be used as a detector system in analytical equipment, including gas and liquid chromatography.

A particular advantage of the microelectrode array detector forming a component of the system of the invention is its disposable nature. That is, because of inexpensive mass production methods, if desired, a new microelectrode array detector can be used for each specific test to be performed. This insures accuracy of the test because the microelectrodes would have pristine surfaces exposed to the solution or environment to be tested.

The uniqueness of the present invention lies largely in the fact that all the necessary elements for a compact sensor—sensing device, electronic equipment, stand-alone computer control of data acquisition and storage, and data analysis methods (pattern recognition) have been combined into a single hand-held, portable device.

The foregoing description of preferred embodiments of the invention have been presented for purposes of illustration and description. It is not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention in various embodiments and with various modifications, as are suited to the particular use contemplated. It is intended that the scope of the invention be defined by the claims appended hereto.

We claim:

1. A method for preparing an electrochemical detector containing microelectrodes embedded in an insulating matrix which comprises:
    (a) selecting a silicon wafer of predetermined size;
    (b) coating one side of said wafer with silicon nitride;
    (c) applying a photo-resist composition to the top of said silicon nitride;
    (d) applying to said photo-resist a mask which selects a predetermined electronic circuit pattern;
    (e) developing said photo-resist;
    (f) evaporating a metal onto the surface of said photo-resist covered wafer to a thickness of about 1000Å.
    (g) lifting off the metal coated photo-resist, leaving a metal circuit pattern on said silicon nitride, and repeating steps (c) through (g) a predetermined number of times with a different metal each time.

2. The method claim 1 wherein said metal evaporated onto the surface of said photo-resist is selected from the group consisting of platinum, gold, carbon, iridium, vanadium, nickel, silver, titanium or copper.

3. The method of claim 1 wherein said photo-resist is deposited to a thickness of 1.25 μm.

4. The method of claim 1 wherein evaporated niobium serves as an adhesion layer between the sensor materials are conductor pattern.

5. The method of claim 1 wherein said unwanted metal is lifted off with acetone.

6. A method of preparing an electrochemical detector containing microelectrodes embedded in an insulating matrix which comprises:
    a. selecting an alumina-ceramic wafer of predetermined size,
    b. coating said wafer on one side with a layer of chromium,
    c. coating said layer of chromium with a layer of gold,
    d. coating said layer of gold with a positive photo-resist composition,
    e. placing a photo-mask with a desired conductor pattern thereon over said photo-resist coated wafer,
    f. exposing said photo-resist coating with ultraviolet light through said photo-mask, and dissolving away those areas of photo-resist not protected from exposure by said photo-mask in a chemical developer bath, exposing said gold,
    g. etching away said gold not covered by said photo-resist, leaving a photo-resist covered gold circuit pattern,
    h. removing the balance of said photo-resist exposing said gold circuit pattern,
    i. depositing a plurality of sensor materials at predetermined areas on said gold circuit pattern, at least one of said sensor materials being platinum,
    j. applying a negative photo-resist over said sensor materials and said wafer,
    k. applying a shadow-mask over said photo-resist covered wafer which has opaque dots corresponding in location with said sensor materials, l. exposing said negative photo-resist to ultraviolet light through said shadow-mask, m. dissolving the unexposed portions of said negative photo-resist corresponding in location with said opaque dots in said shadowmask, thereby leaving exposed to the environment those specific areas of said sensor materials in register with the opaque dots in said shadow mask, thus forming arrays of microelectrodes.

7. The method of claim 6 wherein said sensor materials are selected from the group consisting of platinum, gold, carbon, iridium, vanadium, copper, silver, titanium or nickel.

8. The method of claim 6 wherein said positive photo-resist composition is a photoactive novolak resin in a solvent system.

9. The method of claim 6 wherein said negative photo-resist composition is a photoactive compound in a solvent system.

10. The method of claim 6 wherein said wafer is approximately 10 mil thick, and said chromium is applied to a depth of 0.01 micron.

11. The method of claim 6 wherein said wafer is about 10 mil thick, and said gold is applied to a depth of about 4 microns.

12. The method of claim 6 wherein said gold is etched away with a solution of potassium iodide and iodine crystals.

13. The method of claim 6 wherein said sensor materials are applied to a depth of 0.1–1.0 micron.

14. The method of claim 6 wherein said sensor materials comprise platinum and iridium.

15. The method of claim 6 wherein said sensor materials comprise platinum and vanadium.

16. The method of claim 6 wherein said sensor materials comprise platinum and carbon.

17. The method of claim 6 wherein said microelectrodes are formed of diameter 5 $\mu$m, separated by 14.5 $\mu$m, arranged in arrays of different materials, each comprising a block of approximately 77,000 electrically connected microelectrodes.

18. A method of preparing a wafer containing a plurality of microelectrodes which comprises:

a. selecting a thin alumina-ceramic or silicon wafer of predetermined size, b. adhering to one side of said wafer a conducting material having a predetermined electronic circuit pattern, c. depositing a plurality of different sensor materials at a plurality of predetermined locations on said conducting material, and d. covering said wafer with an inert insulating substance leaving exposed a defined area of said sensor materials, 19. The method of claim 18 wherein the defined area is less than or equal to about 100 $\mu$m$^2$.

20. A method of preparing an electrochemical detector containing microelectrodes embedded in an insulating matrix which comprises:

a. selecting an insulated silicon wafer of predetermined size, b. coating said wafer on one side with a layer of chromium, c. coating said layer of chromium with a layer of gold, d. coating said layer of gold with a positive photo-resist composition, e. placing a photo-mask with a desired conductor pattern thereon over said photo-resist coated wafer, f. exposing said photo-resist coating with ultraviolet light through said photo-mask, and dissolving away those areas of photo-resist not protected from exposure by said photo-mask in a chemical developer bath, exposing said gold, g. etching away said gold not covered by said photo-resist, leaving a photo-resist covered gold circuit pattern, h. removing the balance of said photo-resist exposing said gold circuit pattern, i. depositing a plurality of sensor materials at predetermined areas on said insulating substrate, at least one of said sensor materials being platinum, j. applying a negative photo-resist over said sensor materials and said wafer, k. applying a shadow-mask over said photo-resist covered wafer which has opaque dots corresponding in location with said sensor materials, l. exposing said negative photo-resist through said shadowmask, m. dissolving the unexposed portions of said negative photo-resist corresponding in location with said opaque dots in said shadowmask, thereby leaving exposed to the environment those specific areas of said sensor materials in register with the opaque dots in said shadow mask, thus forming microelectrodes arrays.

21. The method of claim 20 wherein said sensor material is selected from the group consisting of platinum, gold, carbon, iridium, vanadium, copper, silver, nickel, titanium.

22. The method of claim 20 wherein said positive photo-resist composition is a photoactive novolak resin in a solvent system.

23. The method of claim 20 wherein said negative photo resist composition is a photoactive compound in a solvent system.

24. The method of claim 20 wherein said wafer is approximately 10 mil thick, and said chromium is applied to a depth of 0.01 micron.

25. The method of claim 20 wherein said wafer is about 10 mil thick, and said gold is applied to a depth of about 4 microns.

26. The method of claim 20 wherein said gold is etched away with a solution of potassium iodide and iodine crystals.

27. The method of claim 20 wherein said sensor materials are applied to a depth of 0.1–1.0 microns.

28. The method of claim 20 wherein said sensor materials comprise platinum and iridium.

29. The method of claim 20 wherein said sensor materials comprise platinum and vanadium.

* * * * *

UNITED STATES PATENT AND TRADEMARK OFFICE
CERTIFICATE OF CORRECTION

PATENT NO. : 5,296,125

DATED : March 22, 1994

INVENTOR(S) : Robert S. Glass and Dino R. Ciarlo

It is certified that error appears in the above-identified patent and that said Letters Patent is hereby corrected as shown below:

On the title page:

Item [75] "Inventors":

Delete " Sam P. Perone, Pleasanton;".

Delete "James F. Kimmons, Manteca".

Signed and Sealed this

Twenty-ninth Day of August, 1995

*Attest:*

BRUCE LEHMAN

*Attesting Officer*      *Commissioner of Patents and Trademarks*